United States Patent
Osgouei et al.

(10) Patent No.: US 12,098,603 B2
(45) Date of Patent: Sep. 24, 2024

(54) METHOD AND SYSTEM FOR MANAGING CARBON CONTAINING GASES

(71) Applicants: Reza Ettehadi Osgouei, Houston, TX (US); Mehrdad Gharib Shirangi, Houston, TX (US); Qusai A. Darugar, Houston, TX (US); Charles A. Thompason, Jr., Kingwood, TX (US)

(72) Inventors: Reza Ettehadi Osgouei, Houston, TX (US); Mehrdad Gharib Shirangi, Houston, TX (US); Qusai A. Darugar, Houston, TX (US); Charles A. Thompason, Jr., Kingwood, TX (US)

(73) Assignee: BAKER HUGHES OILFIELD OPERATIONS LLC, Houston, TX (US)

( * ) Notice: Subject to any disclaimer, the term of this patent is extended or adjusted under 35 U.S.C. 154(b) by 45 days.

(21) Appl. No.: 17/845,296

(22) Filed: Jun. 21, 2022

(65) Prior Publication Data
US 2023/0407715 A1 Dec. 21, 2023

(51) Int. Cl.
*E21B 21/06* (2006.01)
*B01D 21/26* (2006.01)
(Continued)

(52) U.S. Cl.
CPC .......... *E21B 21/068* (2013.01); *B01D 21/262* (2013.01); *C07D 317/36* (2013.01); *C09K 8/035* (2013.01); *E21B 21/066* (2013.01)

(58) Field of Classification Search
CPC ................................................ E21B 21/06–07
See application file for complete search history.

(56) References Cited

U.S. PATENT DOCUMENTS 4,077,777 A * 3/1978 Henke .................... B01D 53/48
422/616
4,181,494 A 1/1980 Kimberley
(Continued)

FOREIGN PATENT DOCUMENTS

CN 202221255 U 5/2012
CN 111285374 A 6/2020
(Continued)

OTHER PUBLICATIONS

Adeleye, et al.; "Efficient and Greener Synthesis of Propylene Carbonate from CarbonDioxide and Propylene Oxide" ACS publications/I&EC Research; dx.doi.org/10.1021/ie500345z | Ind. Eng. Chem. Res. 2014, 53, 18647-18657; 11 pages.
(Continued)

*Primary Examiner* — Kristyn A Hall
(74) *Attorney, Agent, or Firm* — CANTOR COLBURN LLP

(57) ABSTRACT

A method for managing carbon containing gases, including conveying the carbon containing gas to a reactor vessel, conveying propylene oxide to the vessel, reacting the carbon containing gas with the propylene oxide to create propylene carbonate (PC), applying the propylene carbonate to a cuttings stream from a borehole in a subsurface drilling operation and dissolving residual oil from cuttings of the stream into the propylene carbonate. A system for managing carbon containing gas emissions from a borehole drilling operation, including a carbon containing gas emitter, a reactor vessel fluidly connected to the emitter, a propylene oxide supply fluidly connected to the reactor vessel and an applier connected to the reactor vessel, the applier configured to apply propylene carbonate (PC) created in the reactor vessel to a cuttings stream.

16 Claims, 1 Drawing Sheet

(51) Int. Cl.
*C07D 317/36* (2006.01)
*C09K 8/035* (2006.01)

(56) References Cited

U.S. PATENT DOCUMENTS

| | | | |
|---|---|---|---|
| 4,434,028 A | | 2/1984 | Eppig et al. |
| 5,454,957 A | * | 10/1995 | Roff, Jr. .............. B01F 27/1921 |
| | | | 210/DIG. 5 |
| 6,530,438 B1 | | 3/2003 | Mcintyre |
| 6,763,605 B2 | | 7/2004 | Reddoch |
| 7,306,057 B2 | | 12/2007 | Strong et al. |
| 9,939,197 B2 | | 4/2018 | Hoffman |
| 2008/0047280 A1 | | 2/2008 | Dubar |
| 2010/0155048 A1 | | 6/2010 | Hackett et al. |
| 2016/0046538 A1 | | 2/2016 | Swanson |
| 2019/0390523 A1 | * | 12/2019 | Nguyen ................. G01N 1/286 |
| 2020/0270505 A1 | | 8/2020 | Reddy |

FOREIGN PATENT DOCUMENTS

| | | | | |
|---|---|---|---|---|
| CN | 210796296 U | * | 6/2020 | |
| EP | 3508683 A1 | | 7/2019 | |
| WO | WO-2009016406 A1 | * | 2/2009 | ............... B09B 3/00 |

OTHER PUBLICATIONS

Notification of Transmittal of the International Search Report and the Written Opinion of the International Searching Authority, or the Declaration; PCT/US2023/024527; Mail date: Sep. 20, 2023; 12 pages.

Pierobon et al., "Waste Heat Recovery for Offshore Applications," ASME International Mechanical Engineering Congress and Exposition; Published online Oct. 8, 2013.

* cited by examiner

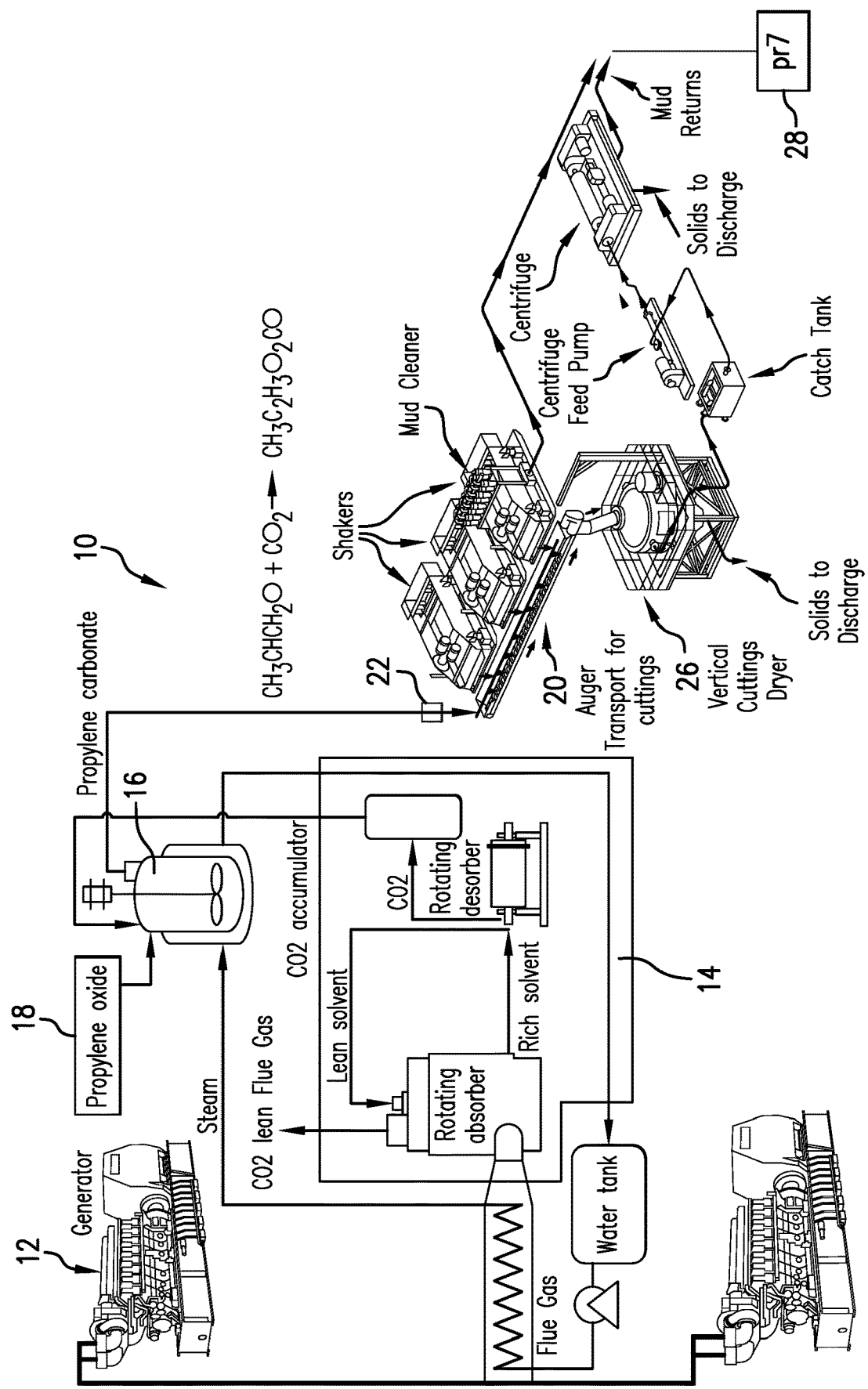

METHOD AND SYSTEM FOR MANAGING CARBON CONTAINING GASES

BACKGROUND

In the resource recovery industry and fluid sequestration industry an uninterrupted power supply is often required at rig sites to support both equipment and human needs. This need is services by large diesel-powered generators. Significant volumes of diesel fuel is used on the order of 20-30 m$^3$ diesel fuel per day according to a leading oil and gas association IPIECA. Unfortunately, a byproduct of generator use is carbon containing gases such as carbon dioxide and carbon monoxide. With a world committed to reducing carbon footprint, additional processes would be welcomed in the art.

SUMMARY

An embodiment of a method for managing carbon containing gases, including conveying the carbon containing gas to a reactor vessel, conveying propylene oxide to the vessel, reacting the carbon containing gas with the propylene oxide to create propylene carbonate (PC), applying the propylene carbonate to a cuttings stream from a borehole in a subsurface drilling operation and dissolving residual oil from cuttings of the stream into the propylene carbonate.

An embodiment of a system for managing carbon containing gas emissions from a borehole drilling operation, including a carbon containing gas emitter, a reactor vessel fluidly connected to the emitter, a propylene oxide supply fluidly connected to the reactor vessel and an applier connected to the reactor vessel, the applier configured to apply propylene carbonate (PC) created in the reactor vessel to a cuttings stream.

BRIEF DESCRIPTION OF THE DRAWINGS

The following descriptions should not be considered limiting in any way. With reference to the accompanying drawings, like elements are numbered alike:

The FIGURE is a schematic view of a system supporting a method disclosed herein.

DETAILED DESCRIPTION

A detailed description of one or more embodiments of the disclosed apparatus and method are presented herein by way of exemplification and not limitation with reference to the FIGURES.

Referring to the FIGURE, a system for reducing carbon containing gas emissions from a borehole drilling operation 10 is in an embodiment a series of components located at a surface location that may be adjacent a borehole (not shown) or could be more remote although transportation of the various components and reactants would increase cost. The system 10 includes a carbon containing gas emitter 12 that may be a power generator in an embodiment. Power generators employed in connection with borehole drilling operations are large and create a significant amount of carbon dioxide as a waste product of the generation of power. Other emitters are also contemplated since it is not the exact type of emitter that is relevant to the invention but rather that something is emitting a carbon containing gas that would become a waste product and through the method disclosed herein is transformed into something useful instead while also eliminating the waste that would have been the case without the method and system disclosed herein. Where the emitter 12 is a power generator, heat is also a waste product that may be captured in connection with the disclosure hereof and used to support chemical reactions and to support other operations, thereby enhancing efficiency of the entire system while reducing escaping waste products of the operation.

The carbon containing gas, emitted from the emitter is captured (and may be concentrated in some embodiments in a concentrating apparatus 14) and fed to a reactor vessel 16. Reactor vessel 16, which in some embodiments is heated by flue gas from the power generator or other heat source, is also fed propylene oxide from a source 18 of propylene oxide. Within the reactor vessel 16 the two components are reformed into propylene carbonate (PC). This is accomplished by reacting the carbon dioxide gas and propylene oxide in the presence of a metal oxide such as La—O or mixed metal oxides such as Ce—La—Zr—O. The reaction is known from American Chemical Society publication "Efficient and Greener Synthesis of Propylene Carbonate from Carbon Dioxide and Propylene Oxide" Ind. Eng. Chem. Res. 2014, 53, 18647-18657. The reaction uses the carbon dioxide and hence converts it to a form that will not be released as a waste product. Accordingly, the conversion to PC is helpful in the fight against climate change.

After creating the PC and reducing carbon dioxide waste release, the PC is conveyed to a stream of cuttings 20 that are exiting the borehole. The cuttings may be exiting the borehole through an auger or through a suction device as is known to the art. The PC is then applied to the cuttings using an applier 22 that may be a spray apparatus in some embodiments. The PC is a solvent and is suited to absorption of residual oil contaminating the cuttings exiting the borehole as well as reducing viscosity and/or density of the oil or oil-based mud on the cuttings. The PC is effective in removing the residual oil from the cuttings and rendering the cuttings acceptably clean for disposal. The PC that was produced using repurposed waste gas is hence used again to benefit another portion of the drilling operation. A cost efficiency is thus realized.

Further, after the residual oil in the cuttings has been dissolved by the PC, the PC (with dissolved oil) is conveyed to a separator 24 where the cuttings are separated from the PC. In embodiments, the separator 24 may be a centrifuge. Heat from the emitter 12 may also be conveyed to the centrifuge to aid in drying of the cuttings. There also may be an additional drier 26.

Once the cuttings are dried and separated form the PC, the cuttings may be disposed of according to local regulation and the PC with the dissolved residual oil becomes an excellent addition to a mud pit/tank 28. The PC mixes with the mud therein and increases volume thereof without any deleterious effect on the mud for drilling purposes.

The system and method as described reduce carbon containing gas waste output and heat waste output at the same improve efficiency of the drilling operation and use the waste products for other gain.

Set forth below are some embodiments of the foregoing disclosure:

Embodiment 1: A method for managing carbon containing gases, including conveying the carbon containing gas to a reactor vessel, conveying propylene oxide to the vessel, reacting the carbon containing gas with the propylene oxide to create propylene carbonate (PC), applying the propylene carbonate to a cuttings stream from a borehole in a subsurface drilling operation and dissolving residual oil from cuttings of the stream into the propylene carbonate.

Embodiment 2: The method as in any prior embodiment wherein the method further comprises heating contents of the reactor vessel.

Embodiment 3: The method as in any prior embodiment wherein the heating is by using waste heat associated with the drilling operation.

Embodiment 4: The method as in any prior embodiment wherein the waste heat is from a generator.

Embodiment 5: The method as in any prior embodiment further separating the propylene carbonate with dissolved residual oil from the cuttings.

Embodiment 6: The method as in any prior embodiment wherein the separating is by spinning the cuttings in a device to centrifugally separate the cuttings from the PC with dissolved residual oil.

Embodiment 7: The method as in any prior embodiment further including drying the cuttings.

Embodiment 8: The method as in any prior embodiment further comprising depositing the propylene carbonate with dissolved residual oil in a mud pit of the drilling operation.

Embodiment 9: The method as in any prior embodiment further including increasing the volume of mud in the mud pit with the PC.

Embodiment 10: The method as in any prior embodiment further including deploying the mud with the PC with dissolved residual oil into the borehole.

Embodiment 11: The method as in any prior embodiment wherein the applying is spraying.

Embodiment 12: A system for managing carbon containing gas emissions from a borehole drilling operation, including a carbon containing gas emitter, a reactor vessel fluidly connected to the emitter, a propylene oxide supply fluidly connected to the reactor vessel and an applier connected to the reactor vessel, the applier configured to apply propylene carbonate (PC) created in the reactor vessel to a cuttings stream.

Embodiment 13: The system as in any prior embodiment wherein the cutting stream is conveyed by a conveyor.

Embodiment 14: The system as in any prior embodiment wherein the conveyor is an auger.

Embodiment 15: The system as in any prior embodiment further comprising a separator to separate the cuttings from the PC with dissolved residual oil.

Embodiment 16: The system as in any prior embodiment wherein the separator is a centrifuge.

Embodiment 17: The system as in any prior embodiment further comprising a mud pit into which separated PC is deposited for combination with drilling mud for redeployment.

Embodiment 18: The system as in any prior embodiment wherein the carbon containing gas emitter is a power generator.

Embodiment 19: The system as in any prior embodiment wherein the applier is a spray device configured and positioned to spray PC on cuttings exiting a borehole created in the borehole drilling operation.

The use of the terms "a" and "an" and "the" and similar referents in the context of describing the invention (especially in the context of the following claims) are to be construed to cover both the singular and the plural, unless otherwise indicated herein or clearly contradicted by context. Further, it should be noted that the terms "first," "second," and the like herein do not denote any order, quantity, or importance, but rather are used to distinguish one element from another. The terms "about", "substantially" and "generally" are intended to include the degree of error associated with measurement of the particular quantity based upon the equipment available at the time of filing the application. For example, "about" and/or "substantially" and/or "generally" can include a range of ±8% or 5%, or 2% of a given value.

The teachings of the present disclosure may be used in a variety of well operations. These operations may involve using one or more treatment agents to treat a formation, the fluids resident in a formation, a borehole, and/or equipment in the borehole, such as production tubing. The treatment agents may be in the form of liquids, gases, solids, semi-solids, and mixtures thereof. Illustrative treatment agents include, but are not limited to, fracturing fluids, acids, steam, water, brine, anti-corrosion agents, cement, permeability modifiers, drilling muds, emulsifiers, demulsifiers, tracers, flow improvers etc. Illustrative well operations include, but are not limited to, hydraulic fracturing, stimulation, tracer injection, cleaning, acidizing, steam injection, water flooding, cementing, etc.

While the invention has been described with reference to an exemplary embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited.

What is claimed is:

1. A method for managing carbon containing gases, comprising:
   conveying the carbon containing gas to a reactor vessel;
   conveying propylene oxide to the vessel;
   reacting the carbon containing gas with the propylene oxide to create propylene carbonate (PC);
   applying the propylene carbonate to a cuttings stream from a borehole in a subsurface drilling operation;
   dissolving residual oil from cuttings of the stream into the propylene carbonate;
   separating the propylene carbonate with dissolved residual oil from the cuttings; and
   depositing the propylene carbonate with dissolved residual oil in a mud pit of the drilling operation thereby increasing a volume of mud in the mud pit.

2. A method for managing carbon containing gases, comprising:
   conveying the carbon containing gas to a reactor vessel
   conveying propylene oxide to the vessel;
   reacting the carbon containing gas with the propylene oxide to create propylene carbonate (PC) including heating contents of the reactor vessel with waste heat from a generator associated with the drilling operation;
   applying the propylene carbonate to a cuttings stream from a borehole in a subsurface drilling operation; and
   dissolving residual oil from cuttings of the stream into the propylene carbonate.

3. A system for managing carbon containing gas emissions from a borehole drilling operation comprising;
   a carbon containing gas emitter;
   a reactor vessel fluidly connected to the emitter;
   a propylene oxide supply fluidly connected to the reactor vessel; and
      an applier connected to the reactor vessel, the applier configured to apply propylene carbonate (PC) created in the reactor vessel to a cuttings stream, the system further comprising a mud pit into which separated PC is deposited for combination with drilling mud for redeployment.

4. The system as claime din claim 3 wherein the cutting stream is conveyed by a conveyor.

5. The system as claimed in claim 4 wherein the conveyor is an auger.

6. The system as claimed in claim 3 further comprising a separator to separate the cuttings from the PC with dissolved residual oil.

7. The system as claimed in claim 6 wherein the separator is a centrifuge.

8. The system as claimed in claim 3 wherein the carbon containing gas emitter is a power generator.

9. The system as claimed in claim 3 wherein the applier is a spray device configured and positioned to spray PC on cuttings exiting a borehole created in the borehole drilling operation.

10. A method for managing carbon containing gases, comprising:
   conveying the carbon containing gas to a reactor vessel;
   conveying propylene oxide to the vessel;
   reacting the carbon containing gas with the propylene oxide to create propylene carbonate (PC);
   applying the propylene carbonate to a cuttings stream from a borehole in a subsurface drilling operation;
   dissolving residual oil from cuttings of the stream into the propylene carbonate;
   separating the propylene carbonate with dissolved residual oil from the cuttings; and
   depositing the propylene carbonate with dissolved residual oil in a mud pit of the drilling operation.

11. The method as claimed in claim 10 wherein the method further comprises heating contents of the reactor vessel.

12. The method as claimed in claim 11 wherein the heating is by using waste heat associated with the drilling operation.

13. The method as claimed in claim 10 wherein the separating is by spinning the cuttings in a device to centrifugally separate the cuttings from the PC with dissolved residual oil.

14. The method as claimed in claim 13 further including drying the cuttings.

15. The method as claimed in claim 10 wherein the applying is spraying.

16. The system as claimed in claim 10 wherein the cutting stream is conveyed by a conveyor.

* * * * *

UNITED STATES PATENT AND TRADEMARK OFFICE
CERTIFICATE OF CORRECTION

PATENT NO. : 12,098,603 B2  
APPLICATION NO. : 17/845296  
DATED : September 24, 2024  
INVENTOR(S) : Reza Ettehadi Osgouei et al.

Page 1 of 1

It is certified that error appears in the above-identified patent and that said Letters Patent is hereby corrected as shown below:

On the Title Page

Item (72):  
Please correct the spelling of Inventor Charles A. Thompason, Jr. to Charles A. Thompson, Jr.

Signed and Sealed this  
Twenty-fourth Day of December, 2024

Derrick Brent  
*Acting Director of the United States Patent and Trademark Office*